(12) United States Patent  
Lee et al.

(10) Patent No.: US 9,395,321 B2  
(45) Date of Patent: Jul. 19, 2016

(54) SAMPLE RECOGNITION METHOD AND BIOSENSOR USING SAME

(71) Applicant: THE BIO CO., LTD, Gyeongsangbuk-do (KR)

(72) Inventors: Young Tae Lee, Andong-si (KR); Seung Ro Lee, Daejeon (KR)

(73) Assignees: THE BIO CO. LTD., Gyeongsangbuk-do (KR); Seung Ro Lee, Yuseong-gu (KR)

( * ) Notice: Subject to any disclaimer, the term of this patent is extended or adjusted under 35 U.S.C. 154(b) by 0 days.

(21) Appl. No.: 14/663,008

(22) Filed: Mar. 19, 2015

(65) Prior Publication Data

US 2015/0198555 A1 Jul. 16, 2015

Related U.S. Application Data

(63) Continuation of application No. PCT/KR2012/007591, filed on Sep. 21, 2012.

(51) Int. Cl.

| | |
|---|---|
| *G01N 27/327* | (2006.01) |
| *G01N 27/22* | (2006.01) |
| *A61B 5/145* | (2006.01) |
| *A61B 5/1486* | (2006.01) |
| *C12Q 1/00* | (2006.01) |
| *A61B 5/15* | (2006.01) |
| *B01L 3/00* | (2006.01) |

(52) U.S. Cl.
CPC ............ *G01N 27/327* (2013.01); *A61B 5/1486* (2013.01); *A61B 5/14532* (2013.01); *C12Q 1/001* (2013.01); *C12Q 1/006* (2013.01); *G01N 27/227* (2013.01); *G01N 27/3272* (2013.01); *G01N 27/3273* (2013.01); *A61B 5/150358* (2013.01); *B01L 3/502715* (2013.01); *G01N 2333/90* (2013.01)

(58) Field of Classification Search
CPC .. G01N 27/327; G01N 27/3272; G01N 27/22
See application file for complete search history.

(56) References Cited

U.S. PATENT DOCUMENTS

2008/0060196 A1* 3/2008 Wang ................. G01N 27/3272 29/854
2010/0089775 A1 4/2010 Chen et al.

FOREIGN PATENT DOCUMENTS

| EP | 0 732 406 A1 | 9/1996 |
|---|---|---|
| JP | 2004-4017 A | 1/2004 |
| KR | 10-2010-0042399 A | 4/2010 |
| KR | 10-0998648 B1 | 12/2010 |

OTHER PUBLICATIONS

International Search Report issued for corresponding International Patent Application No. PCT/KR2012/007591, mailed on Apr. 29, 2013.

* cited by examiner

*Primary Examiner* — Alexander Noguerola
(74) *Attorney, Agent, or Firm* — Myers Wolin, LLC.

(57) ABSTRACT

A biosensor and a method for recognizing a liquid sample are provided, which can recognize whether a sample is introduced by recognizing an inside of a sample introduction channel through measurement of capacitance. The biosensor includes an upper plate and a lower plate facing each other, a middle plate interposed between the upper plate and the lower plate to form a sample introduction channel through a recess portion, a working electrode and an auxiliary electrode formed in the sample introduction channel, a sample recognition electrode formed on an outside of the sample introduction channel in a position that corresponds to the sample introduction channel, and a capacitance measurement portion electrically connected to any one of the working electrode and the auxiliary electrode and the sample recognition electrode.

21 Claims, 10 Drawing Sheets

SAMPLE RECOGNITION METHOD AND BIOSENSOR USING SAME

CROSS-REFERENCE TO RELATED APPLICATION

This application claims priority from and the benefit of International Patent Application No. PCT/KR2012/007591, filed on Sep. 21, 2012, which is incorporated herein by reference for all purposes as if fully set forth herein.

BACKGROUND

1. Field

Exemplary embodiments of the invention relate to a method for recognizing whether a sample is introduced through measurement of a capacitance difference and a biosensor using the method.

2. Background

Recently, there has been increasing concern about biosensors that diagnose the state of a person tested through measurement of a biological sample.

Particularly, in diagnosing and preventing diabetes, the necessity of periodic monitoring of glucose concentrations in blood has been increased. Currently, each and every person can easily measure blood glucose using a strip type biosensor that is in the form of a hand-held portable measurement unit.

Recently commercialized biosensors measure blood glucose in a blood sample using the electrochemical principle, which is as follows.

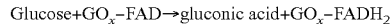

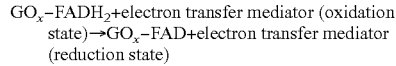

In the above-described reaction formulas, $GO_x$ denotes glucose oxidase, and $GO_x$–FAD and $GO_x$–$FADH_2$ denote an oxidation state and a reduction state of FAD (Flavin Adenine Dinucleotide) that is an active region of glucose oxidase, respectively.

The above-described measurements should be performed in a state where sufficient blood fills in an introduction channel in which working electrodes are provided. Otherwise, measurement error may occur. Accordingly, it is necessary to accurately grasp a time point when blood (sample) sufficiently fills in the introduction channel.

In the related art, a blood recognition electrode is exposedly arranged in a channel to which blood is introduced to primarily measure a signal that indicates whether the blood is introduced. That is, when a blood arrival signal is acquired, a voltage is primarily applied to acquire a current signal. However, the residual current signal that is caused by the primarily applied voltage may exert an influence on the measurement of the glucose concentrations when the glucose concentrations are measured by secondarily applying a measurement voltage to a working electrode and a reference electrode for actual measurement of the glucose concentrations at the next stage. Due to this, a fatal problem may occur on the accuracy and repeated implementation of the electrochemical biosensor.

SUMMARY

Accordingly, the invention has been made to solve the above-mentioned problems occurring in the related art, and a subject to be achieved by the invention is to provide a biosensor which can measure a change of permittivity in a sample introduction channel, which occurs due to an introduction of a liquid sample into the sample introduction channel, through a change of capacitance.

Another subject to be achieved by the invention is to provide a method for recognizing whether a sample is introduced by confirming a change of permittivity in a sample introduction channel through measurement of capacitance of the sample introduction channel.

Additional advantages, subjects, and features of the invention will be set forth in part in the description which follows and in part will become apparent to those having ordinary skill in the art upon examination of the following or may be learned from practice of the invention.

In one aspect of the invention, there is provided a biosensor, which includes an upper plate and a lower plate facing each other; a middle plate interposed between the upper plate and the lower plate to form a sample introduction channel through a recess portion; a working electrode and an auxiliary electrode formed in the sample introduction channel; a sample recognition electrode formed on an outside of the sample introduction channel in a position that corresponds to the sample introduction channel; and a capacitance measurement portion electrically connected to any one of the working electrode and the auxiliary electrode and the sample recognition electrode.

In another aspect of the invention, there is provided a biosensor, which includes an upper plate and a lower plate facing each other; a middle plate interposed between the upper plate and the lower plate to form a sample introduction channel through a recess portion; a working electrode and an auxiliary electrode formed in the sample introduction channel; a pair of sample recognition electrodes formed on an outside of the sample introduction channel in a position that corresponds to the sample introduction channel; and a capacitance measurement portion electrically connected to the sample recognition electrodes.

In still another aspect of the invention, there is provided a biosensor, which includes an upper plate and a lower plate facing each other; a middle plate interposed between the upper plate and the lower plate to form a sample introduction channel through a recess portion; a working electrode and an auxiliary electrode formed in the sample introduction channel; and a capacitance measurement portion electrically connected to any one of the working electrode and the auxiliary electrode and the upper plate.

In yet still another aspect of the invention, there is provided a method for recognizing a liquid sample, which includes preparing a first electrode and a second electrode which is spaced apart from the first electrode and defines a sample introduction channel portion in a gap space between the first electrode and the second electrode; putting a liquid sample into the sample channel portion; and measuring capacitance between the first electrode and the second electrode.

Detailed items of other embodiments are included in the detailed description and drawings.

According to embodiments of the invention, at least the following effects can be achieved. That is, according to the biosensor and the method for recognizing a liquid sample according to the invention, in the case where the interior materials in the sample introduction channel are the sample and air, it can be recognized whether the sample is sufficiently introduced into the sample introduction channel through measurement of the change of capacitance that is caused by the difference in permittivity between the interior materials in the sample introduction channel.

The effects of the invention are not limited to the above-described effects, and other unmentioned effects will be clearly understood to those skilled in the art from the description of claims.

BRIEF DESCRIPTION OF THE DRAWINGS

The above and other subjects, features and advantages of the invention will be more apparent from the following detailed description taken in conjunction with the accompanying drawings, in which.

DETAILED DESCRIPTION OF THE ILLUSTRATED EMBODIMENTS

Figure 1:
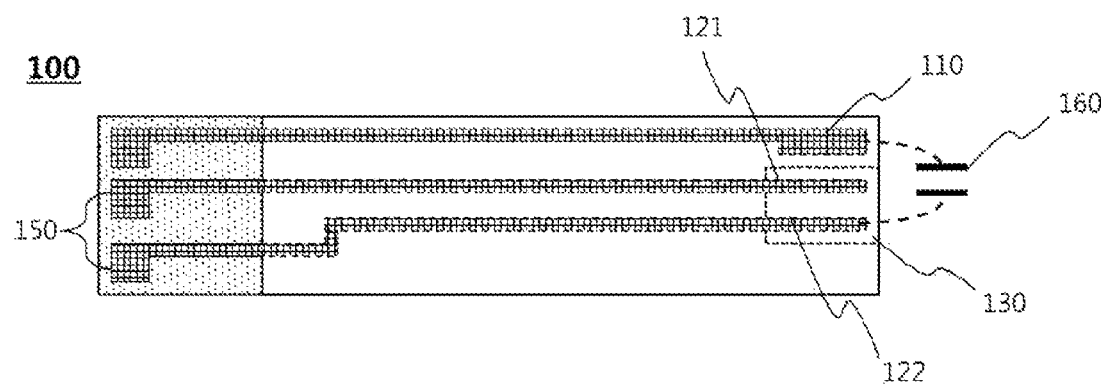
FIG. 1 is a schematic planar projection view of a biosensor according to an embodiment of the invention.

Advantages and features of the invention and methods of accomplishing the drawings in detail below with reference to embodiments that will be apparent. However, the invention is disclosed below, rather than being limited to the exemplary embodiments will be implemented in many different forms, these embodiments are that the present disclosure is complete, and the invention is of ordinary skill in the art to those fully inform the scope of the invention which would provide for, the invention will only be defined by the appended claims.

Element (elements) or a layer or layers of the other elements "on" is referred to as the middle of or immediately above the other elements or other element is sandwiched by another layer includes both cases. Throughout the specification reference numerals refer to the components.

Although the first, second, etc. are used to describe various components, but these components are not limited by those terms as well. These terms are only one component with the other components that will be used to distinguish. Therefore, in the following referred to in the first component is within the technical spirit of the invention the second component may work as well.

Hereinafter, embodiments of the invention will be described with reference to the accompanying drawings.

Figure 2:
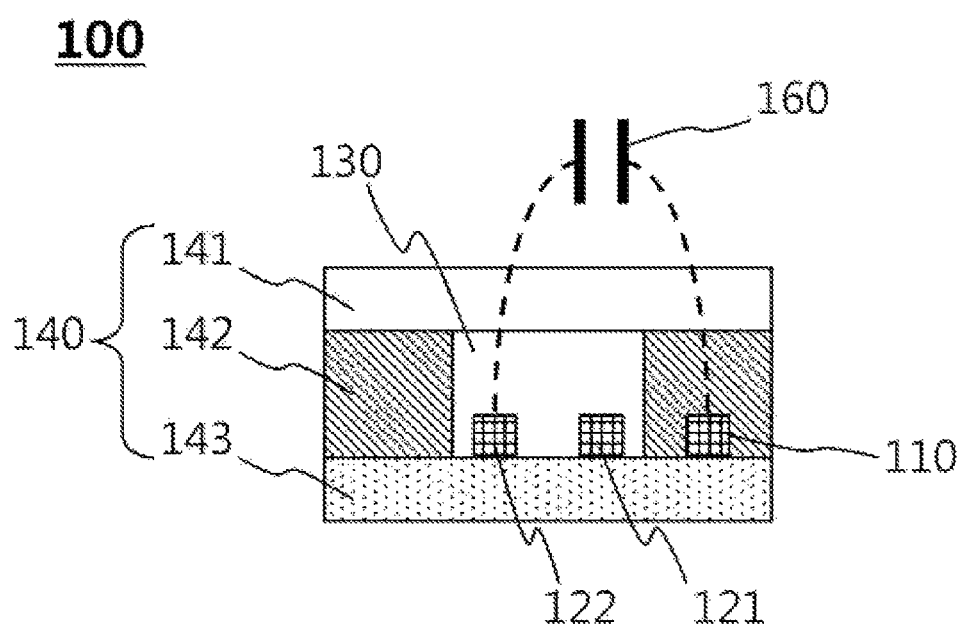
FIG. 2 is a vertical cross-sectional view of the biosensor of FIG. 1.

FIG. 1 is a schematic planar projection view of a biosensor according to an embodiment of the invention, and FIG. 2 is a vertical cross-sectional view of the biosensor of FIG. 1. Referring to FIGS. 1 and 2, a biosensor 100 includes an upper plate 141 and a lower plate 143 facing each other; a middle plate 142 interposed between the upper plate 141 and the lower plate 143 to form a sample introduction channel 130 through a recess portion; a working electrode 121 and an auxiliary electrode 122 formed in the sample introduction channel 130; a sample recognition electrode 110 positioned on an inside of the middle plate 142 on a side surface of the sample introduction channel 130; and a capacitance measurement portion 160 electrically connected to the auxiliary electrode 122 and the sample recognition electrode 110.

The upper plate 141 and the lower plate 143 may be made of an insulating material. The kind of the material of the upper plate 141 and the lower plate 143 is not limited in so far as it is an insulating material. For example, the upper plate 141 and the lower plate 143 may be thin plates made of PET, PVC, or polycarbonate.

The middle plate 142 may be made of an insulating material in the same manner as the upper plate 141 and the lower plate 143. As an example, the middle plate 142 may be interposed between the upper plate 141 and the lower plate 143 and may serve to bond the upper plate 141 and the lower plate 143 to each other. As such a bonding means, the middle plate 142 may be composed of a double sided tape. Further, the middle plate 142 includes the recess portion for forming the sample introduction channel 130.

In a position that corresponds to the recess portion of the middle plate 142, the working electrode 121 and the auxiliary electrode 122 are formed on the surface of the upper portion of the lower plate 143. The working electrode 121 is an electrode by which an electron transfer mediator that is included in a reaction sample layer (not illustrated) is oxidized or reduced. By applying a constant voltage to the working electrode 121 on the basis of the auxiliary electrode 122, the electron transfer mediator that is in a reduction state is oxidized, and an analyzed material in the sample can be quantified through measurement of the amount of oxidization current generated at that time.

The working electrode 121 and the auxiliary electrode 122 may be connected to opposite ends of the biosensor 100 through lead wires. If the biosensor 100 is inserted into a separate measurement device (not illustrated), the oxidization current is transferred into the measurement device through the lead wires, and thus the concentration of the analyzed material may be measured through measurement of the oxidization current.

The working electrode 121 and the auxiliary electrode 122 may be produced using carbon, graphite, platinum processed carbon, silver, gold, palladium, or platinum components. As an example, the working electrode 121 may be printed on the lower plate 143 using ink composed of carbon or platinum processed carbon or ink including palladium. As another example, the working electrode may be formed on the lower substrate by vapor deposition using gold. The lead wires may be made of the same component as the electrodes 121 and 122, or may be made of a separate conductive material.

As an example, the lower plate 143 may be a printed circuit board (PCB) on which the working electrode 121 and the auxiliary electrode 122 are printed.

In the drawings, it is illustrated that both the working electrode 121 and the auxiliary electrode 122 are formed on the surface of the upper portion of the lower plate 143, but are not limited thereto. The working electrode 121 and the auxiliary electrode 122 may be formed anywhere in the blood introduction channel 130.

The sample recognition electrode 110 is positioned on one side surface of the sample introduction channel 130 inside the middle plate 142 in a position that corresponds to the sample introduction channel 130. Such a configuration is merely exemplary, and the sample recognition electrode 110 may also be positioned on an outer surface of the middle plate 142 of the sample recognition electrode 110.

The capacitance measurement portion 160 is configured to be electrically connected to the auxiliary electrode 122 and the sample recognition electrode 110. Through the capacitance formed between the auxiliary electrode 122 and the sample recognition electrode 110, the change of permittivity in the sample introduction channel 130 can be measured, and through this, it can be recognized whether the sample is sufficiently introduced into the channel.

Further, the capacitance measurement portion 160 may be electrically connected to the working electrode 121 and the sample recognition electrode 110.

The capacitance may be represented by $C=\epsilon A/d$, that is, "(relative permittivity of a material between electrode plates*area of the electrode plates)/(distance between the electrode plates)". Here, each material has its own relative permittivity, and if the same distance and the same area are set, the capacitance and the relative permittivity are in proportion to each other. The relative permittivity may differ depending on the state or the concentration of the material, and preferably, it may be an average permittivity.

A partial region of the middle plate 142 may be provided between the auxiliary electrode 122 and the sample recognition electrode 110 in addition to the region of the sample introduction channel 130. However, the permittivity and the thickness of the partial region of the middle plate 142 are not changed, and thus do not exert an influence on the recognition of whether the sample is introduced.

The sample recognition electrode 110 may be connected to an end of the opposite side of the biosensor 100. As an example, the sample recognition electrode 110 may be electrically connected to the capacitance measurement portion 160 through the lead wires.

The liquid sample of the biosensor 100, although the kind thereof is not limited, may be, for example, blood, and the biosensor may be a biosensor for measuring blood glucose.

Figure 3:
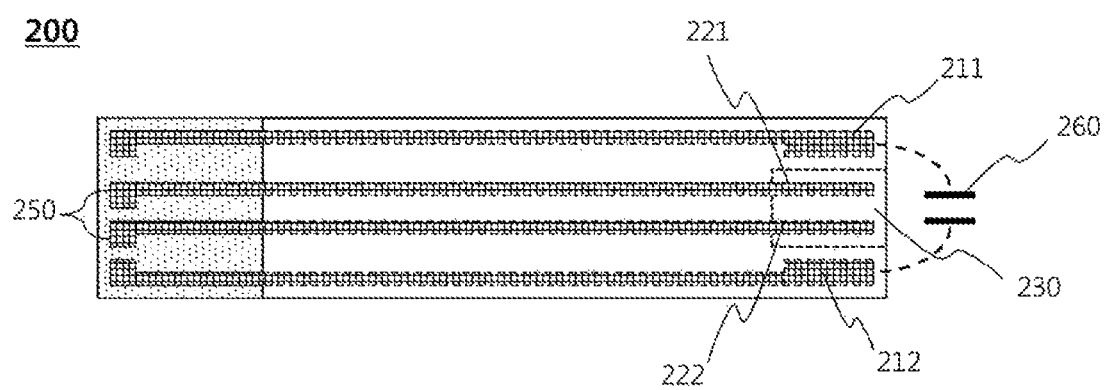
FIG. 3 is a schematic planar projection view of a biosensor according to another embodiment of the invention.
Figure 4:
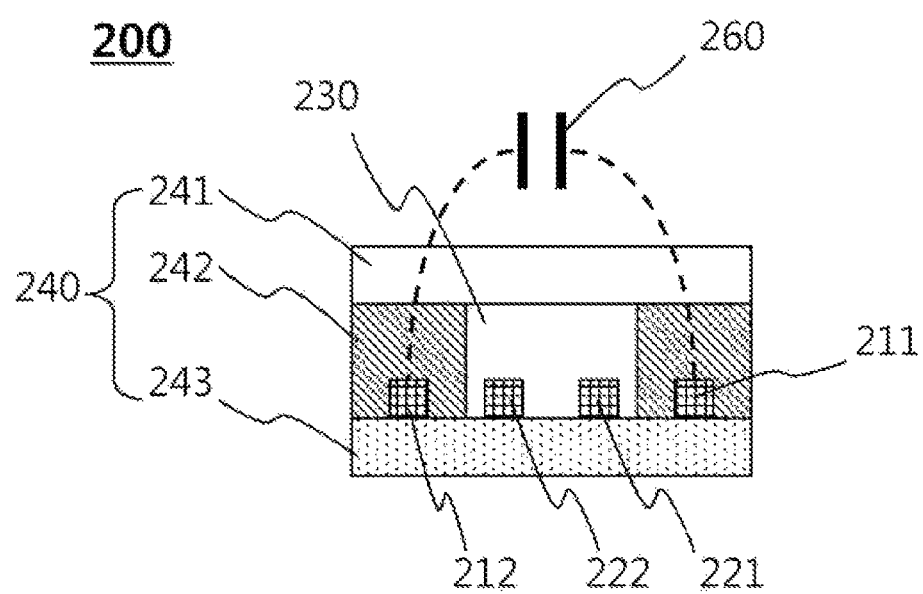
FIG. 4 is a vertical cross-sectional view of the biosensor of FIG. 3.

FIG. 3 is a schematic planar projection view of a biosensor according to another embodiment of the invention, and FIG. 4 is a vertical cross-sectional view of the biosensor of FIG. 3. Referring to FIGS. 3 and 4, a biosensor 200 includes an upper plate 241 and a lower plate 243 facing each other; a middle plate 242 interposed between the upper plate 241 and the lower plate 243 to form a sample introduction channel 230 through a recess portion; a working electrode 221 and an auxiliary electrode 222 formed in the sample introduction channel 230; a pair of sample recognition electrodes 211 and 212 formed on an outside of the sample introduction channel 230 in a position that corresponds to the sample introduction channel 230; and a capacitance measurement portion 260 electrically connected to the sample recognition electrodes 211 and 212.

The biosensor 200 has the same basic configuration as that of the biosensor 100 of FIGS. 1 and 2, but is different from the biosensor 100 on the point that it has a pair of sample recognition electrodes 211 and 212.

The sample recognition electrodes 211 and 212 are positioned on both side surfaces of the sample introduction channel 230 inside the middle plate 242 in a position that corresponds to the sample introduction channel 230. Such a configuration is merely exemplary, and the sample recognition electrodes 211 and 212 may also be positioned on outer surfaces of both sides of the middle plate 242.

The capacitance measurement portion 260 is configured to be electrically connected to the first sample recognition electrode 211 and the second sample recognition electrode 212. Through the capacitance formed between the first sample recognition electrode 211 and the second sample recognition electrode 212, the change of permittivity in the sample introduction channel 230 can be measured, and through this, it can be recognized whether the sample is sufficiently introduced into the channel.

A partial region of the middle plate 242 may be provided between the first sample recognition electrode 211 and the second sample recognition electrode 212 in addition to the region of the sample introduction channel 230. However, the permittivity and the thickness of the partial region of the middle plate 242 are not changed, and thus do not exert an influence on the recognition of whether the sample is introduced.

Figure 5:
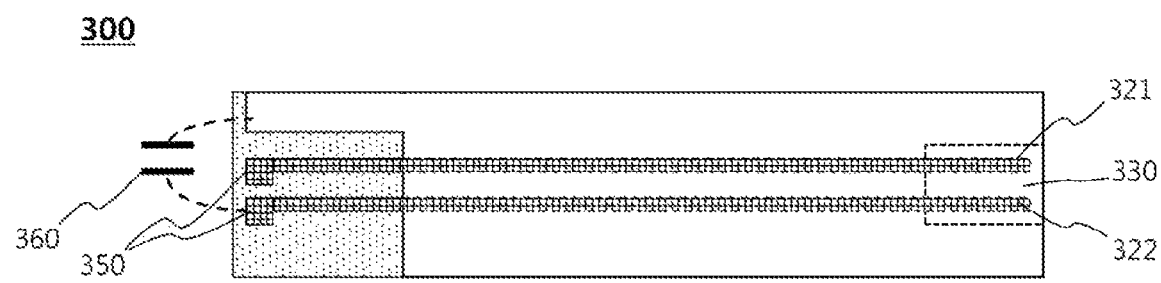
FIG. 5 is a schematic planar projection view of a biosensor according to still another embodiment of the invention.
Figure 6:
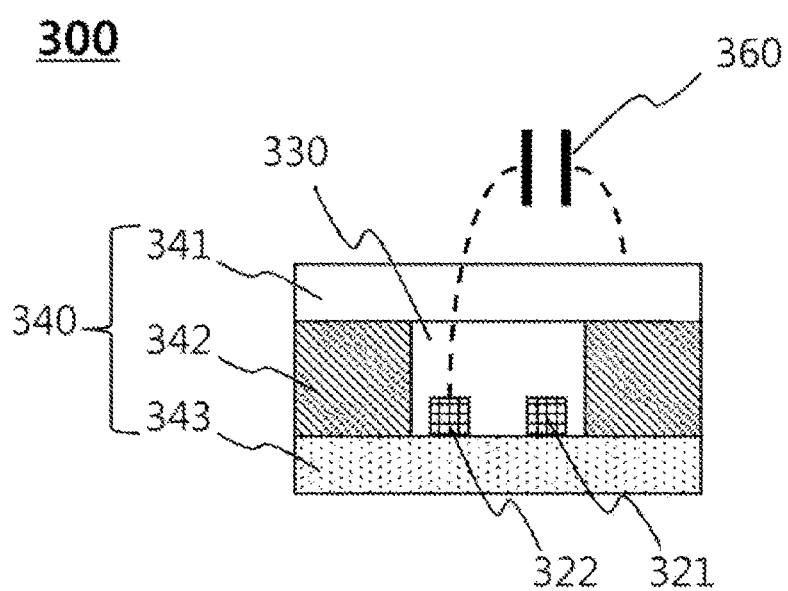
FIG. 6 is a vertical cross-sectional view of the biosensor of FIG. 5.

FIG. 5 is a schematic planar projection view of a biosensor according to still another embodiment of the invention, and FIG. 6 is a vertical cross-sectional view of the biosensor of FIG. 5. Referring to FIGS. 5 and 6, a biosensor 300 includes an upper plate 341 and a lower plate 342 facing each other; a middle plate 342 interposed between the upper plate 341 and the lower plate 342 to form a sample introduction channel 330 through a recess portion; a working electrode 321 and an auxiliary electrode 322 formed in the sample introduction channel 330; and a capacitance measurement portion 360 electrically connected to any one of the working electrode 321 and the auxiliary electrode 322 and the upper plate 341.

The biosensor 300 senses the change of permittivity in the sample introduction channel 330 through measurement of capacitance between the auxiliary electrode 322 and the upper plate 341 through the capacitance measurement portion 360. Such a configuration is merely exemplary, and the capacitance measurement portion 360 may be electrically connected to the working electrode 321 and the upper plate 341. Further, in accordance with the position of the working electrode 321 or the auxiliary electrode 322 in the sample introduction channel 330, the capacitance measurement portion 360 may be electrically connected to the working electrode 321 or the auxiliary electrode 322 and the opposite plate.

Water having permittivity that is similar to the permittivity of blood was injected into the sample introduction channel 330 of the biosensor 300, and the capacitance difference between the auxiliary electrode 322 and the upper plate 341 before and after the water injection was measured by frequencies was measured. The result of the measurement is shown in FIG. 7 and Table 1 below.

TABLE 1

| Frequency (kHz) | Before water injection (pF) | After water injection (pF) | Signal difference (pF) |
|---|---|---|---|
| 1 | 7.65 | 11.2 | 3.55 |
| 10 | 7.58 | 11.44 | 3.86 |
| 100 | 8.28 | 12.15 | 3.87 |
| 300 | 10.3 | 15.13 | 4.83 |
| 500 | 13.8 | 20.3 | 6.5 |
| 700 | 17.77 | 26.27 | 8.5 |
| 1000 | 21.87 | 32.8 | 10.93 |
| 1500 | 26 | 39.8 | 13.8 |
| 2000 | 25.07 | 40 | 14.93 |
| 2500 | 26.47 | 41.7 | 15.23 |
| 3000 | 29.53 | 47.43 | 17.9 |
| 4000 | 32.77 | 51.83 | 19.06 |
| 5000 | 34.2 | 54.53 | 20.33 |

Figure 7:
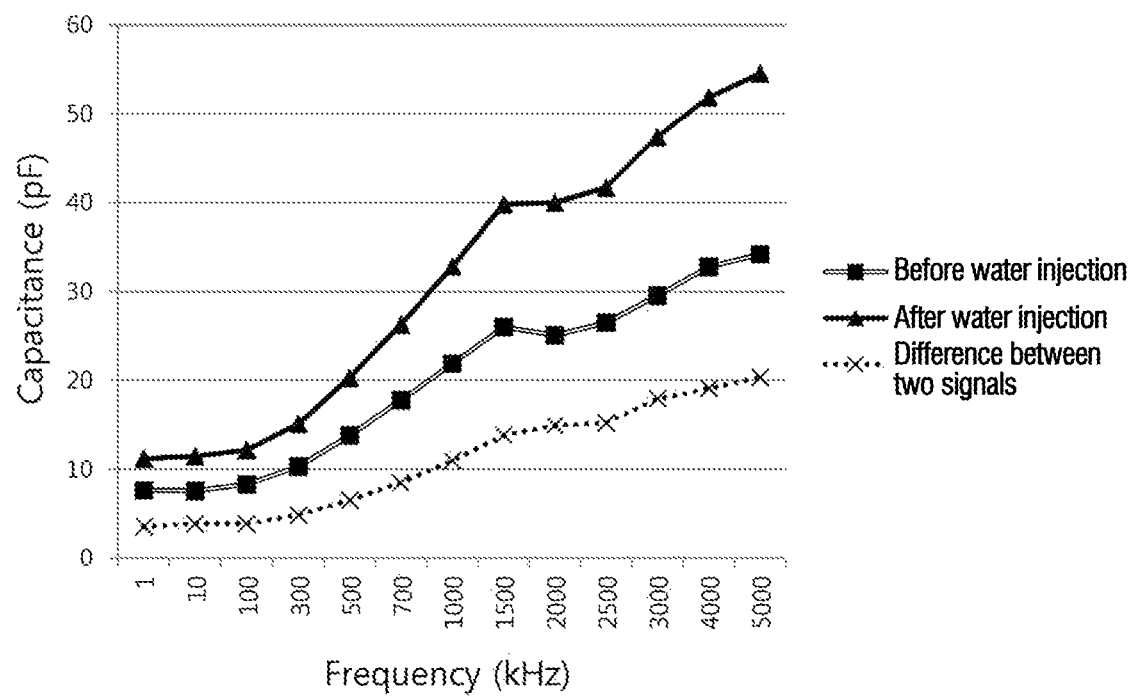
FIG. 7 is a graph illustrating a capacitance difference measured before and after water injection into the biosensor of FIGS. 5 and 6.

Referring to FIG. 7 and Table 1 as above, as the frequency is increased, the capacitance difference before and after the water injection becomes greater, and the capacitance difference at a frequency of 1 kHz becomes distinctive, that is, 3.55 pF. Accordingly, it can be confirmed that the sample can be recognized in the entire experimental frequency range.

Figure 8:
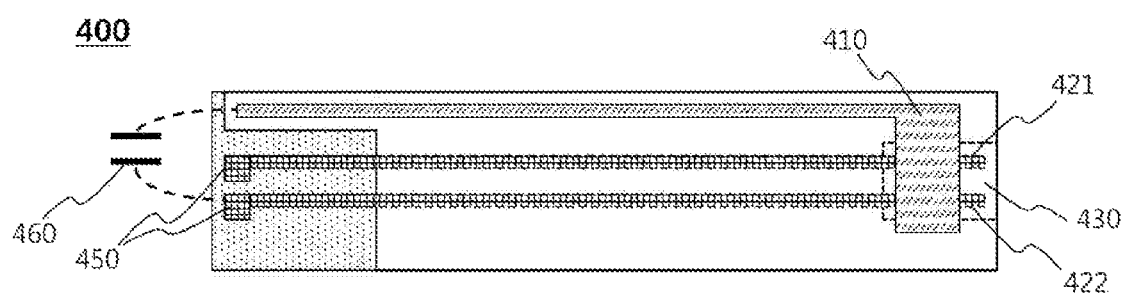
FIG. 8 is a schematic plan view of a biosensor according to an embodiment of the invention.
Figure 9:
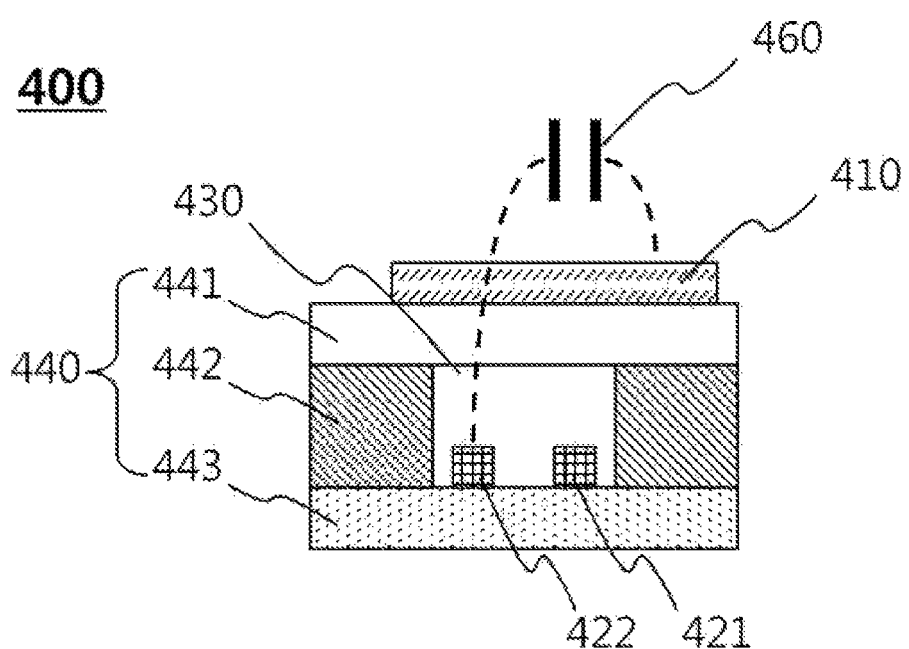
FIG. 9 is a vertical cross-sectional view of the biosensor of FIG. 8.

FIG. 8 is a schematic plan view of a biosensor according to an embodiment of the invention, and FIG. 9 is a vertical cross-sectional view of the biosensor of FIG. 8. Referring to FIGS. 8 and 9, a biosensor 400 includes an upper plate 441 and a lower plate 443 facing each other; a middle plate 442 interposed between the upper plate 441 and the lower plate 443 to form a sample introduction channel 430 through a recess portion; a working electrode 421 and an auxiliary electrode 422 formed in the sample introduction channel 430; a sample recognition electrode 410 positioned on an surface of an upper portion of the upper plate 441 on an upper surface of the sample introduction channel 430; and a capacitance measurement portion 460 electrically connected to the auxiliary electrode 422 and the sample recognition electrode 410.

The sample recognition electrode 410 may be manufactured by a general method for manufacturing an electrode. Preferably, the upper plate 441 may be a printed circuit board (PCB) on which the sample recognition electrode 410 is printed. In this case, a separate process is not required after the upper plate 441 is manufactured, and thus the biosensor 400 can be manufactured without addition of a separate process.

Water having permittivity that is similar to the permittivity of blood was injected into the sample introduction channel 430 of the biosensor 400, and the capacitance difference between the auxiliary electrode 422 and the electrode 410 that is positioned on the upper plate 441 before and after the water injection was measured by frequencies was measured. The result of the measurement is shown in FIG. 10 and Table 2 below.

TABLE 2

| Frequency (kHz) | Before water injection (pF) | After water injection (pF) | Signal difference (pF) |
|---|---|---|---|
| 1 | 8.6 | 14.43 | 5.83 |
| 10 | 8.93 | 14.4 | 5.47 |
| 100 | 9.1 | 15 | 5.9 |
| 300 | 11.13 | 18.87 | 7.74 |
| 500 | 14.07 | 22.7 | 8.63 |
| 700 | 18 | 29.87 | 11.87 |
| 1000 | 22.33 | 38.83 | 16.5 |
| 1500 | 26.13 | 49.17 | 23.04 |
| 2000 | 27.4 | 55.7 | 28.3 |
| 2500 | 30 | 55.13 | 25.13 |
| 3000 | 30.7 | 60.53 | 29.83 |
| 4000 | 33.07 | 64.6 | 31.53 |
| 5000 | 34.57 | 68.17 | 33.6 |

Figure 10:
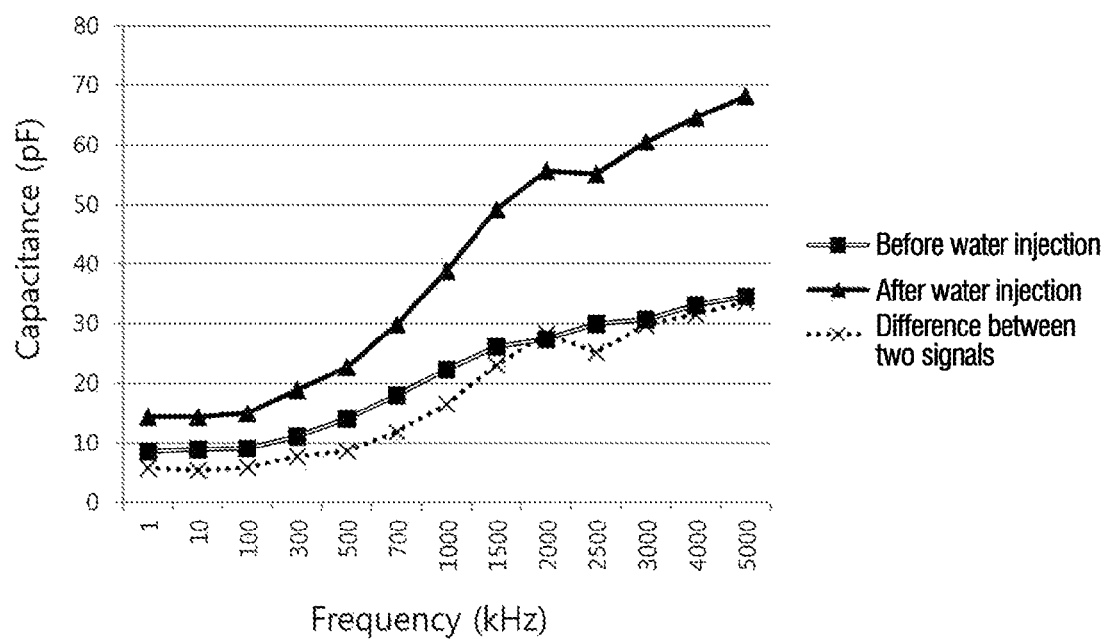
FIG. 10 is a graph illustrating a capacitance difference measured before and after water injection into the biosensor of FIGS. 8 and 9.

Referring to FIG. 10 and Table 2 as above, as the frequency is increased, the capacitance difference before and after the water injection becomes greater, and the capacitance difference at a frequency of 1 kHz becomes distinctive, that is, 5.83 pF. Accordingly, it can be confirmed that the sample can be recognized in the entire experimental frequency range.

Although preferred embodiments of the invention have been described for illustrative purposes, those skilled in the art will appreciate that various modifications, additions and substitutions are possible, without departing from the scope and spirit of the invention as disclosed in the accompanying claims.

What is claimed is:

1. A biosensor comprising:
   an upper plate and a lower plate facing each other;
   a middle plate interposed between the upper plate and the lower plate to form a sample introduction channel through a recess portion;
   a working electrode and an auxiliary electrode formed in the sample introduction channel;
   a sample recognition electrode formed on an outside of the sample introduction channel in a position that is along a side surface of the sample introduction channel; and
   a capacitance measurement portion electrically connected to the sample recognition electrode and to any one of the working electrode and the auxiliary electrode.

2. The biosensor of claim 1, wherein the sample recognition electrode is positioned on an inside of the middle plate on a side surface of the sample introduction channel.

3. The biosensor of claim 1, wherein the sample recognition electrode is positioned on an outer surface of the middle plate on a side surface of the sample introduction channel.

4. The biosensor of claim 1, wherein the sample recognition electrode is positioned on an upper surface of the upper plate on an upper surface of the sample introduction channel.

5. The biosensor of claim 1, wherein the sample recognition electrode is positioned on an inside of the upper plate on an upper surface of the sample introduction channel.

6. The biosensor of claim 1, wherein the working electrode and the auxiliary electrode are formed on an upper surface of the lower plate.

7. The biosensor of claim 1, wherein the working electrode and the auxiliary electrode are arranged in parallel to each other.

8. The biosensor of claim 1, wherein the sample recognition electrode is arranged in parallel to the working electrode and the auxiliary electrode.

9. The biosensor of claim 1, further comprising a reaction sample layer formed on a surface of the working electrode and including an oxidase and an electron transfer mediator.

10. A biosensor comprising:
    an upper plate and a lower plate facing each other;
    a middle plate interposed between the upper plate and the lower plate to form a sample introduction channel through a recess portion;
    a working electrode and an auxiliary electrode formed in the sample introduction channel;
    a pair of sample recognition electrodes formed on an outside of the sample introduction channel in a position that corresponds to the sample introduction channel; and
    a capacitance measurement portion electrically connected to the sample recognition electrodes.

11. The biosensor of claim 10, wherein the sample recognition electrodes are arranged in parallel to each other.

12. The biosensor of claim 10, wherein the working electrode and the auxiliary electrode are formed on an upper surface of the lower plate.

13. The biosensor of claim 10, wherein the working electrode and the auxiliary electrode are arranged in parallel to each other.

14. The biosensor of claim 10, further comprising a reaction sample layer formed on a surface of the working electrode and including an oxidase and an electron transfer mediator.

15. A biosensor comprising:
    an upper plate and a lower plate facing each other;
    a middle plate interposed between the upper plate and the lower plate to form a sample introduction channel through a recess portion;
    a working electrode and an auxiliary electrode formed in the sample introduction channel; and
    a capacitance measurement portion electrically connected to the upper plate and to any one of the working electrode and the auxiliary electrode.

16. The biosensor of claim 15, wherein the working electrode and the auxiliary electrode are arranged in parallel to each other.

17. The biosensor of claim 15, further comprising a reaction sample layer formed on a surface of the working electrode and including an oxidase and an electron transfer mediator.

18. A method for recognizing a liquid sample, comprising;
defining a sample introduction channel portion in a gap space;
providing a first electrode and a second electrode which is spaced apart from the first electrode, at least one of the first and second electrodes being formed on the outside of the sample introduction channel portion in a position that is along a side surface of the sample introduction channel portion;
putting a liquid sample into the sample channel portion; and
measuring capacitance between the first electrode and the second electrode.

19. The method of claim 18, wherein the first electrode is a working electrode or an auxiliary electrode, and the second electrode is a sample recognition electrode that is arranged in parallel to the first electrode in a position that corresponds to the sample introduction channel portion.

20. The method of claim 18, wherein the first electrode and the second electrode are sample recognition electrodes that are arranged in parallel to each other on both side surfaces of the sample introduction channel portion.

21. The biosensor of claim 15, wherein the working electrode and the auxiliary electrode are formed on an upper surface of the lower plate.

\* \* \* \* \*